United States Patent [19]

Kreider

[11] 3,954,768

[45] May 4, 1976

[54] 2-(2-METHYL-5-NITRO-1-IMIDAZOLYL)ETHYL CYCLOAMINOCARBODITHIOATES

[75] Inventor: Eunice M. Kreider, Chicago, Ill.

[73] Assignee: G. D. Searle & Co., Chicago, Ill.

[22] Filed: Apr. 23, 1974

[21] Appl. No.: 463,295

Related U.S. Application Data

[63] Continuation-in-part of Ser. No. 268,749, July 3, 1972, abandoned.

[52] U.S. Cl. .................. 260/268 H; 260/247.1 M; 260/293.7; 424/248; 424/251; 424/267
[51] Int. Cl.² .................................. C07D 295/14
[58] Field of Search ........ 260/309, 247.1 M, 268 H, 260/293.7

[56] References Cited
UNITED STATES PATENTS

| 3,376,311 | 4/1968 | Butler | 260/309 |
|---|---|---|---|
| 3,458,528 | 7/1969 | Gal | 260/309 |
| 3,646,027 | 2/1972 | Carlson et al. | 260/309 X |
| 3,696,116 | 10/1972 | Jeanmart et al. | 260/309 |
| 3,723,453 | 3/1973 | Gradnik et al. | 260/309 |
| 3,803,165 | 4/1974 | Beaman et al. | 260/309 |
| 3,828,065 | 8/1974 | Kreider | 260/309 |

FOREIGN PATENTS OR APPLICATIONS 2,035,573  2/1971  Germany

OTHER PUBLICATIONS

Conaut et al., The Chemistry of Organic Compounds, 3rd Ed.; p. 342 (1947).

Primary Examiner—Lorraine A. Weinberger
Assistant Examiner—Michael Shippen
Attorney, Agent, or Firm—John J. McDonnell

[57] ABSTRACT 2-(2-Methyl-5-nitro-1-imidazolyl)ethyl esters of cycloaminocarbodithioates are herein described. These compounds are anti-protozoal and anti-fungal agents. The compounds are prepared in 2 steps. The reaction of the appropriate cycloamine with carbon disulfide in aqueous base forms the aminocarbodithioate salt and the final products are formed by the reaction of this salt with 1-(2-chloroethyl)-2-methyl-5-nitroimidazole.

3 Claims, No Drawings

2-(2-METHYL-5-NITRO-1-IMIDAZOLYL)ETHYL CYCLOAMINOCARBODITHIOATES

This is a continuation in part of my copending U.S. application Ser. No. 268,749, filed July 3, 1972 now abandoned.

The present invention relates to a group of 2-(2-methyl-5-nitro-1-imidazolyl)ethylcycloaminocarbodithioate esters having the following general formula

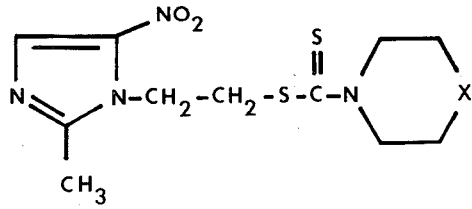

wherein X is oxygen, imino, lower alkyl imino, $\beta$-hydroxyethylimino, methylene, lower alkyl methylene, or $\beta$-hydroxyethylmethylene. Lower alkyl contains 1–7 carbon atoms.

Thus are formed the morpholino, piperazinyl, N-(lower alkyl)piperazinyl, N-(2-hydroxyethyl)piperazinyl, piperidino, 2-lower alkyl piperidino, and 4-(2hydroxyethyl)piperidino radicals, respectively.

The compounds of the present invention are useful in view of their anti-biotic activity. They are especially effective in inhibiting the growth of protozoa.

Evidence of the anti-protozoal utility of the present compounds is obtained from standardized tests designed to determine the capacity of test compounds to inhibit the growth of *Trichomonas vaginalis*. These tests are carried out in the following manner. A modified Diamond medium is prepared by mixing 1200 parts of trypticase (Baltimore Biological Laboratories), 600 parts of yeast extract (Difco), 300 parts of maltose, 60 parts of L-cysteine hydrochloride, 12 parts of L-ascorbic acid, 48 parts of dibasic potassium phosphate, 48 parts of monobasic potassium phosphate and 54,000 parts of distilled water. The pH is adjusted to 6.8 with 40% sodium hydroxide solution and 30 parts of agar (Baltimore Biological Laboratories) is incorporated. The mixture is boiled for one minute to dissolve the agar and is then sterilized in an autoclave. To 80 volumes of the resultant medium is aseptically added 20 volumes of sterile Dubos medium serum. The resultant medium is inoculated with 1% by volume of a 72-hour culture of *T. vaginalis*, whereupon 1 ml. of the inoculated medium is mixed with 10 mg. of test compound. The mixture is incubated anaerobically at 37°C. for 48 hours and then examined microscopically for the present of motile trichomonads. If any are observed the compound is considered inactive. If no motile trichomonads are observed, 0.1 ml. of the incubated mixture is serially diluted and mixed with additional quantities of the inoculated medium sufficient to produce concentrations of 1000, 100, 10 and 1 micrograms of test compound per ml. and the resulting mixtures are incubated anaerobically as before at 37°C. for 48 hours and then examined microscopically for the present of motile trichomonads. Controls are provided by concurrent incubation identical with the foregoing except for the absence of test compound.

The anti-protozoal activity is further evidenced by activity against *Tetrahymena pyriformis*. A nutrient broth consisting of 12 gm. of proteose peptone, 8 gm. of sucrose, and 500 ml. of water was sterilized and inoculated with 10% (by volume) of an axenic culture of *Tetrahymena pyriformis*. Meanwhile, compound was heated in sterile distilled water at a concentration of 2000 μg. per ml. and a temperature of 80°C. for 20 min. An equivolume mixture of this compound preparation and the inoculated medium was incubated aerobically at 32°C. for 48 hr. and then examined microscopically for the presence of motile tetrahymena. If no motile tetrahymena were observed, the incubated mixture was serially diluted and mixed with an inoculated medium of the same composition as that described above excepting that 1000 ml. of distilled water instead of 500 ml. and 5% (by volume) of the culture instead of 10% were incorporated. Amounts of the latter medium added were such that concentrations of 100, 10 and 1 μg. of compound per ml. resulted. The mixtures thus obtained were incubated as before and then examined microscopically for motile tetrahymena. Controls were provided by concurrent incubations identical with the foregoing except for the absence of compound.

The anti-fungal activity of the present compounds is evidenced by their activity against *Bacillus subtilis*. Nutrient broth (manufactured by Baltimore Biological Laboratories or Difco) was prepared twice the concentration recommended by the manufacturer, sterilized, and inoculated with 2% (by volume) of a culture of *Bacillus subtilis*. Meanwhile, compound was heated in sterile distilled water at a concentration of 2000 μg. per ml. and a temperature of 80°C. for 20 min. An equivolume mixture of this compound preparation and the inoculated broth was incubated aerobically at 37°C. and then examined grossly for growth of the test organism. The incubation period was 20–24 hr. If growth of the test organism was observed, the compound was considered inactive. If no such growth was observed, the incubated mixture was serially diluted and mixed with an inoculated broth of the same composition as before excepting that the concentration was halved and 1% (by volume) of the culture instead of 2% was incorporated. Amounts of the latter broth added were such that concentrations of 100, 10 and 1 μg. of compound per ml. resulted. The mixtures thus obtained were incubated as before and then examined grossly for growth of the test organism. Potency is expressed as the minimum concentration at which no growth of test organism is discernible. Controls were provided by concurrent incubations identical with the foregoing except for the absence of compound.

These compounds are prepared by the general approach shown in Scheme A.

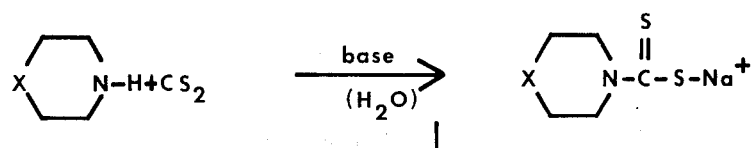

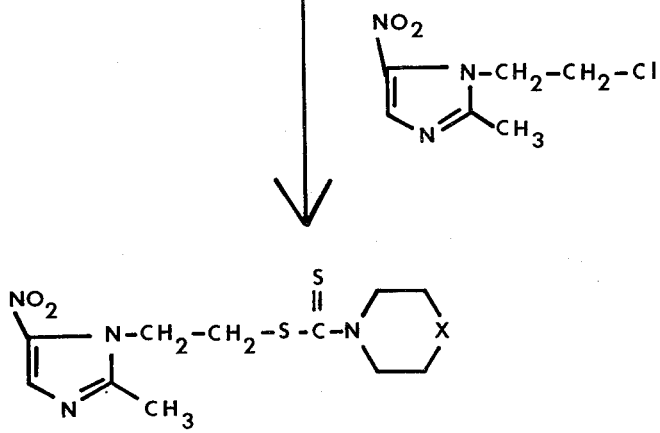

Scheme A

Carbon disulfide is added to an aqueous basic solution of a given amine and the resulting dithiocarbamate salt is isolated as shown in the first step of Scheme A. Some of the salts are commercially available. Solutions of dithiocarbamate salts in polar solvents and 1-(2-chloroethyl)-2-methyl-5-nitroimidazole (*J. Med. Chem.*, 11, 370 (1968)) are reacted in the presence of sodium or potassium iodide to form the corresponding 2(2-methyl-5-nitro-1-imidazolyl)ethyl dithiocarbamates as shown in the second step of Scheme A. For instance, when carbon disulfide is added to an aqueous sodium hydroxide solution of 4-β-hydroxyethylpiperazine, sodium 4-(2-hydroxyethyl)-1-piperazinylcarbodithioate is formed and when a solution of this salt in dimethylformamide or dimethylsulfoxide is reacted with 1-(2-chloroethyl)-2-methyl-5-nitroimidazole, 2-(2-methyl-5-nitroimidazolyl)ethyl-4-(2-hydroxyethyl)-1-piperazinylcarbodithioate is obtained.

The following examples are presented to further illustrate the present invention. They should not be construed as limiting it either in spirit or in scope. In these examples quantities are indicated in parts by weight unless parts by volume are specified, and temperatures are indicated in degrees Centigrade (°C.). The relationship between parts by weight and parts by volume is the same as that existing between grams and milliliters.

The reaction mixture is stirred in a cold bath until a heavy precipitate results. After cooling for an additional hour, the precipitate is filtered, washed with ether and vacuum dried. The resulting sodium 4-(2-hydroxyethyl)-1-piperazinylcarbodithioate was used without further purification.

A solution of 2.2 parts of 1-(2-chloroethyl)-2-methyl-5-nitroimidazole and 1.2 parts of sodium iodide in 25 parts by volume of dimethylformamide is prepared and added to a solution of 3.0 parts of sodium 4-(2-hydroxyethyl)-1-piperazinylcarbodithioate as prepared above, in 25 parts by volume of dimethylformamide. The reaction mixture is stirred at room temperature under anhydrous conditions for 24 hours, diluted with 100 parts by volume of water and extracted with chloroform. The chloroform solution is washed with water and dried over anhydrous sodium sulfate. The sodium is filtered and the solution is concentrated to a volume of approximately 25 parts by volume. The addition of 5 parts by volume of hexane followed by cooling provides a precipitate. The precipitate is isolated and dissolved in hot 50% ethyl acetate-50% hexane containing decolorizing charcoal. The solution is further heated and the charcoal is filtered. Cooling provides crystals of 2-(2-methyl-5-nitro-1-imidazolyl)ethyl-4-(2-hydroxyethyl)-1-piperazinylcarbodithioate, melting at 127-128.5°. This compound is represented by the following formula

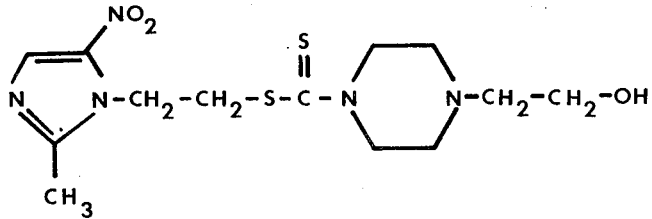

EXAMPLE 1

To a solution of 4 parts sodium hydroxide in 10 parts by volume of H₂O is added 13 parts of 4-hydroxyethylpiperazine. The solution is stirred in an ice bath during slow addition of 10 parts by volume of carbon disulfide.

EXAMPLE 2

Sodium-(4-methyl)-1-piperazinylcarbodithioate is prepared in the manner described in Example 1, using N-methylpiperazine as the amine. A solution of 2.77 parts of this salt in 25 parts by volume of dimethylformamide is reacted with a solution of 1.3 parts of sodium iodide and 2.27 parts of 1-(2-chloroethyl)-2-methyl-5-nitroimidazole in 25 parts by volume of dimethylformamide, as described in Example 1. This procedure provides 2-(2-methyl-5-nitro-1-imidazolyl)ethyl-4-methyl-1-piperazinylcarbodithioate, melting at 120°–122°. This compound is represented by the following formula

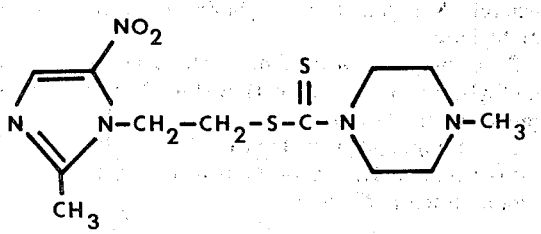

EXAMPLE 3

Sodium-1-piperidinocarbodithioate is prepared in the manner described in Example 1, using piperidine as the amine. A solution of 3.11 parts of this salt in 25 parts by volume of dimethylformamide is reacted with a solution of 1.55 parts of sodium iodide and 2.84 parts of 1-(2-chloroethyl)-2-methyl-5-nitroimidazole in 25 parts by volume of dimethylformamide, as described in Example 1. This procedure provides 2-(2-methyl-5-nitro-1-imidazolyl)ethyl-1-piperidinocarbodithioate, melting at 102°–102.5°. The formula for this compound is

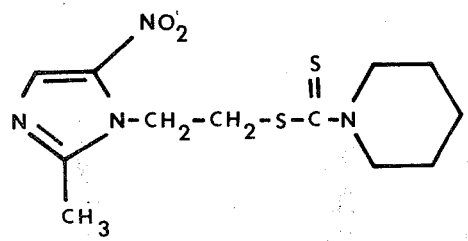

EXAMPLE 4

Sodium 4-(2-hydroxyethyl)-1-piperidinocarbodithioate is prepared in the manner described in Example 1, using 4-(2-hydroxyethyl piperidine) as the amine. A solution of 3.40 parts of this salt in 25 parts by volume of dimethylformamide is reacted with a solution of 1.2 parts of sodium iodide and 2.27 parts of 1-(2-chloroethyl)-2-methyl-5-nitroimidazole in 25 parts by volume of dimethylformamaide, as described in Example 1. This procedure provides 2-(2-methyl-5-nitro-1-imidazolyl)ethyl-4-(2-hydroxyethyl)-1-piperidinocarbodithioate, melting at 142°–144.5°. The formula for this compound is

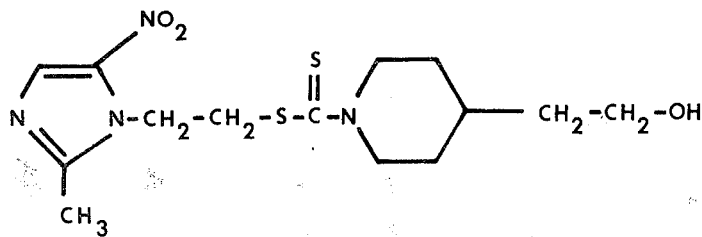

EXAMPLE 5

Sodium 1-morpholinocarbodithioate is prepared in the manner described in Example 1, using morpholine as the amine. A solution of 2.78 parts of this salt in 25 parts by volume of dimethylformamide is reacted with a solution of 1.5 parts of sodium iodide and 2.85 parts of 1-(2-chloroethyl)-2-methyl-5-nitroimidazole in 25 parts by volume of dimethylformamide, as described in Example 1. This procedure provides 2-(2-methyl-5-nitro-1-imidazolyl)ethyl-1-morpholinocarbodithioate, melting at 133°–135.5°. The formula for this compound is

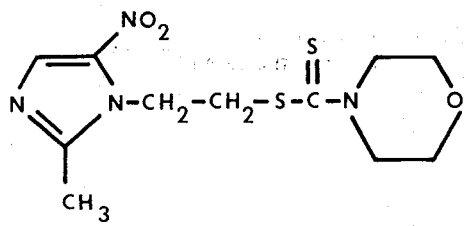

EXAMPLE 6

Sodium-4-ethyl-1-piperidinocarbodithioate is prepared in the manner described in Example 1, using 4-ethylpiperidine as the amine. A solution of 3.00 parts of this salt in 25 parts by volume of dimethylformamide is reacted with a solution of 1.2 parts of sodium iodide and 2.27 parts of 1-(2-chloroethyl)-2-methyl-5-nitroimidazole in 25 parts by volume of dimethylformamide as described in Example 1. This procedure provides 2-(2-methyl-5-nitro-1-imidazolyl)ethyl-4-ethyl-1-piperidinocarbodithioate. The formula for this compound is

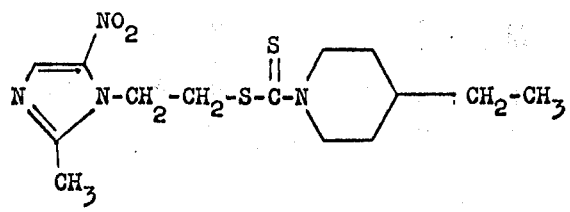

EXAMPLE 7

Sodium-1-piperazinylcarbodithioate is prepared in the manner described in Example 1, using piperazine as the amine. A solution of 2.77 parts of this salt in 25 parts by volume of dimethylformamide is reacted with a solution of 1.3 parts of sodium iodide and 2.27 parts of 1-(2-chloroethyl)-2-methyl-5-nitroimidazole in 25 parts by volume of dimethylformamide as described in Example 1. This procedure provides 2-(2-methyl-5-nitro-1-imidazolyl)ethyl-1-piperazinylcarbodithioate. This compound is represented by the following formula

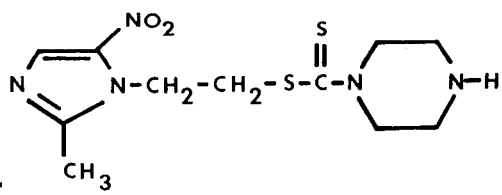

What is claimed is:
1. A compound of the formula

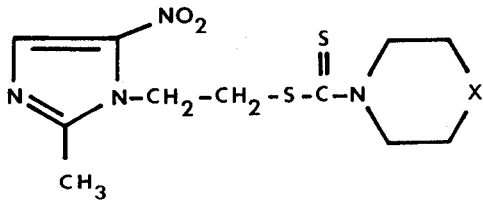

wherein X is β-hydroxyethylimino or β-hydroxyethylmethylene.

2. A compound according to claim 1, which is 2-(2-methyl-5-nitro-1-imidazolyl)ethyl-4-(2-hydroxyethyl)-piperazinylcarbodithioate.

3. A compound as in claim 1, which is 2-(2-methyl-5-nitro-1-imidazolyl)ethyl-4-(2-hydroxyethyl)-piperidinocarbodithioate.

* * * * *